US008557311B2

(12) United States Patent
Wu et al.

(10) Patent No.: US 8,557,311 B2
(45) Date of Patent: Oct. 15, 2013

(54) GYNOSTEMMA EXTRACT SURFACTANT/CLEANING AGENT/EMULSIFIER/FOAMING AGENT AND METHOD OF PRODUCING SAME

(75) Inventors: Jerry Wu, San Jose, CA (US); Brien Quirk, Eugene, OR (US)

(73) Assignee: DRACO Natural Products, San Jose, CA (US)

( * ) Notice: Subject to any disclaimer, the term of this patent is extended or adjusted under 35 U.S.C. 154(b) by 627 days.

(21) Appl. No.: 12/616,687

(22) Filed: Nov. 11, 2009

(65) Prior Publication Data
US 2010/0119469 A1 May 13, 2010

Related U.S. Application Data

(60) Provisional application No. 61/113,888, filed on Nov. 12, 2008.

(51) Int. Cl.
*A61K 36/424* (2006.01)
(52) U.S. Cl.
USPC ............ 424/758; 424/401; 424/725; 510/130
(58) Field of Classification Search
USPC .......................................... 424/725, 401, 758
See application file for complete search history.

(56) References Cited

U.S. PATENT DOCUMENTS 5,658,578 A * 8/1997 Ogawa et al. .................. 424/401
5,910,308 A   6/1999 D'Jang
6,051,154 A   4/2000 Meyer
7,232,585 B2  6/2007 Quan et al.

FOREIGN PATENT DOCUMENTS

| JP | 61050907 A | * | 3/1986 |
| JP | 08099858 A | * | 4/1996 |
| JP | 2007051091 A | * | 3/2007 |
| WO | WO 9962478 A1 | * | 9/1999 |

OTHER PUBLICATIONS

Poucher's Perfumes, Cosmetics and Soaps, 2000, Springer-Verlag, (10th Ed by Hilda Butler), p. 413-450.*
Flick, E., Cosmetic and Toiletry Formulations, 1996, Noyes Publications, vol. 3, 2nd ed., p. 8.*
JP 2007-051091 A, Mar. 2007, machine translation.*
JP 08-099858 A, Apr. 1996, machine translation.*
Yuchi, S. et al. "Cosmetic composition containing extract of gynostemma penetaphyllum makino", Mar. 13, 1986, JP361050907A, abstract.*
Schreiner, V. et al. "Cosmetic or dermatologic preparations containing catechins or green tea extract", Dec. 9, 1999, abstract.*
Kim et al., "Cosmetic composition or pharmaceutical composition for skin whitening . . . ", Sep. 24, 2008, KR 2008085292 A, abstract.*
Arita, S. "Cosmetic product compoistion that contains gynostemma pentaphyllum makino extract", JP 61050907 A, Mar. 13, 1986, English translation (PTO 12-2730).*

Li H, Lee JH, Ha JM. Effective purification of ginsenosides from cultured wild ginseng roots,red ginseng, and white ginseng with macroporous resins. J Microbiol Biotechnol. Nov. 2008;18(11):1789-91.
Liu F, Ren D, Guo DA, Pan Y, Zhang H, Hu P. Method development for gypenosides fingerprint by high performance liquid chromatography with diode-array detection and the addition of internal standard. Chem Pharm Bull (Tokyo). Mar. 2008; 56(3):389-93.
Chang CK, Chang KS, Lin YC, Liu SY, Chen CY. Hairy root cultures of *Gynostemma pentaphyllum* (Thunb.) Makino: a promising approach for the production of gypenosides as an altenative of ginseng saponins. Biotechnol Lett. Aug. 2005;27(16):1165-9.
Huang TH, Tran VH, Roufogalis BD, Li Y. Gypenoside XLIX, a naturally occuring gynosaponin, PPAR-alpha dependently inhibits LPS-induced tissue factor expression and activity in human THP-1 monocytic cells. Toxicol Appl Pharmacol. Jan. 1, 2007;218(1):30-6. Epub Oct. 25, 2006.
Ding SL, Zhu ZY. [Studies on chemical constituents of *Gynostemma compressum*]. Yao Xue Xue Bao. 1993; 28(5):364-9.
Hu L, Chen Z, Xie Y. New triterpenoid saponins from *Gynostemma pentaphyllum*. J Nat Prod. Dec. 1996;59(12):1143-5. Guo XL, Wang TJ, Bian BL. [Studies on the chemical constituents of *Gynostemma longipes* C.Y. Wu]. Yao Xue Xue Bao. Jul. 1997;32(7):524-9. Abstract provided (1 page).
Hui RH, Hou DY, Li TC, Liu XY. [Simultaneous determination of total flavone and total saponin in *Gynostemma pentaphyllum* by signal multiplier spectrophotometry]. Guang Pu Xue Yu Guang Pu Fen Xi. Sep. 2006;26(9):1753-6. Abstract provided (1 page).
Kao TH, Huang SC, Inbaraj BS, Chen BH. Determination of flavonoids and saponins in *Gynostemma pentaphyllum* (Thunb.) Makino by liquid chromatography-mass spectrometry. Anal Chim Acta. Sep. 26, 2008;626(2):200-11. Epub Aug. 8, 2008.
Xiang WJ, Guo CY, Ma L, Hu LH. Dammarane-type glycosides and long chain sesquiterpene glycosides from *Gynostemma yixingense*. Fitoterapia. Sep. 23, 2009 [Epub ahead of print], pp. 1-5.
Yang Z, Chen Q, Hu L. Dammarane-type glycosides from *Gynostemma pubescens*. Phytochemistry. Jul. 2007;68 (13):1752-61. Epub Jun. 15, 2007.
Yin F, Hu L, Lou F, Pan R. Dammarane-type glycosides from *Gynostemma pentaphyllum*. J Nat Prod. Jun. 2004;67(6):942-52.
Yin F, Zhang YN, Yang ZY, Hu LH. Nine new dammarane saponins from *Gynostemma pentaphyllum*. Chem Biodivers. Jul. 2006;3(7):771-82.

(Continued)

*Primary Examiner* — Gina C Justice
(74) *Attorney, Agent, or Firm* — Zheng Jin

(57) ABSTRACT

*Gynostemma* extract compositions containing *gynostemma* extract and at least a carrier liquid are used as cleaning agents, emulsifiers, skin care products, and foaming agents. The *gynostemma* extract alone or together with other herbal extracts is mixed with water, glycerin, or a mixture of water and glycerin to produce the surfactant composition. The extracts have distinctive surface tension altering functions, reducing the surface tension of aqueous solutions and allowing foam formation, micelle formation, and emulsification with oil, dirt and water insoluble substances, and may also be used as an emulsification agent with other ingredients in cosmetic or personal care products.

7 Claims, No Drawings

(56) References Cited

OTHER PUBLICATIONS

Yin F, Zhang Y, Yang Z, Cheng Q, Hu L. Triterpene saponins from *Gynostemma cardiospermum*. J Nat Prod. Oct. 2006;69(10):1394-8.
Guo XL, Wang TJ, Bian BL. [Studies on the chemical constituents of *Gynostemma longipes* C.Y. Wu]. Yao Xue Xue Bao. Jul. 1997;32(7):524-9. Abstract provided (1 page).
Wei J, Chen Y, Cao S. [Saponins in the fruit pedicels of *Panax notoginseng* (Burk.) F.H. Chen (continue)]. Zhongguo Zhong Yao Za Zhi. Oct. 1992;17(10):611-3, 639-40 concl. Abstract provided (1 page).
Ding, Shu-Li et al. Gycomoside I: A New Dammarane Saponin from *Gynostemma compressum*. Planta Med. Aug. 1993;59(4):373-5.
Tanaka, Osamu et al. Saponins of Plants of *Panax* Species Collected in Central Nepal, and Their Chemotaxonomical Significance. III, Pharmaceutical Society of Japan. Chem. Pharm. Bull. 48(6) 889-892 (2000), Jun. 2000.
Cheeke, Peter R. Ph.D., Saponins: Surprising Benefits of Desert Plants, http://lpi.oregonstate.edu/sp-su98/saponins.html, last updated May 1998. The Linus Pauling Institute, 4 pages.
Chinese soapberry website. Product information. http://www.soapberry.org. copyright 2007. 3 pages.
Stoffels, Karin. Soap Nut Saponins Create Powerful Natural Surfactant, Personal Care Ingredients Formulation Manufacture. http://www.personalcaremagazine.com/Print.aspx?Story=4325. Sep. 2008. 2 pages.

* cited by examiner

GYNOSTEMMA EXTRACT SURFACTANT/CLEANING AGENT/EMULSIFIER/FOAMING AGENT AND METHOD OF PRODUCING SAME

RELATED APPLICATIONS

The present application claims the benefit of co-pending U.S. provisional patent application No. 61/113,888, filed on Nov. 12, 2008, the contents of which are incorporated herein by reference in their entirely.

BACKGROUND

1. Field of the Invention

This invention relates generally to a *gynostemma* extract surfactant for use in cleaning agents, emulsifiers, foaming agents and the like, and a method for producing the same.

2. Related Art

Surfactants are generally defined as materials that can greatly reduce the surface tension of water even when used in very low concentrations. A surfactant works by reducing the surface tension of the washing solvent, such as water, so that non-polar oils and insoluble dirt can be dissolved or dispersed by polar water molecules. It generally contains non-polar regions of its molecules to attract a non-polar substance like oil by way of molecular attractive forces. The surfactant also contains a polar region of its molecule which will allow it to be solvated or surrounded by polar water molecules thereby dispersing the oil or dirt into the aqueous medium to be washed away. The surfactant will form a micelle or spherical structure in which the oil molecule is completely surrounded by the non-polar region of the surfactant molecular, while the polar end of the molecule faces outward forming loose hydrogen bonding and stabilization with water molecules.

One common use of a surfactant is in sanitary applications as a cleaning agent where dirt and oils are removed from surface areas such as skin, hairs, and household furnishings. Another common use of a surfactant is in the manufacture of skin-care products as an emulsifier in a base solution for the active ingredients.

Currently, harsh chemical detergents like sodium dodecyl sulfate (sodium lauryl sulfate) and harsh traditional soaps are common surfactants in the manufacture of cleaning and emulsifying products. Chemical detergents have been found irritating and harsh in removing oily substances from the human body skin. These chemical detergents may contain traces of unwanted harmful chemicals especially when they are derived from non-renewable petrochemical sources. Additionally, a possible link to skin cancer has been found with sodium lauryl sulfate, a surfactant, when combined with mineral oil in moisturizer lotions.

Accordingly, there is a need for milder, non-synthetic, renewable, naturally-occurring surfactants, which can provide beneficial effects to skin with reduced irritation.

SUMMARY

The present invention provides for plant extract products containing saponins from the leaves and stems of plants of the *gynostemma* genus, which contain large amounts of dammarane saponins (hereinafter referred to as "saponins"), polysaccharides, and other phytocompounds, either alone or together with extracts from other plants containing saponins *Gynostemma* extracts in a carrier liquid provide natural surfactant compositions which may be used as personal care products and cleaning agents. The extract has distinctive surface tension altering functions, which reduce the surface tension of aqueous solutions and allow foam formation and emulsification with oil, dirt and water insoluble substances. A solution with as low as 0.1% *gynostemma* extract by weight containing at least 10% by weight of saponins can be used as a surfactant in a cleaning agent, foaming agent, emulsifying agent, skin care products, or the like.

In one embodiment, a natural surfactant composition is provided which comprises at least 0.1% by weight of *gynostemma* extract in a solution of water, glycerin, or glycerin and water, either alone or together with other natural ingredients. The amount of *gynostemma* extract in the solution may be in the range from 0.1% to 20%. The *gynostemma* extract contains at least 10% by weight of saponins, and may contain up to 99% by weight of saponins. This composition has high foaming capability even in hard water, and the foam is long-lasting, making it suitable for various cleaning and personal care products, including foaming bubble bath and shaving cream formulations. In one embodiment, a foaming shaving cream composition comprised 0.1 to 0.5% *gynostemma* extract, 69.5% to 69.9% glycerin, and 30% water.

In another embodiment, a topical skin care composition was provided, comprising 10% by weight *gynostemma* extract, 5% by weight green tea, 5% by weight *panax ginseng*, and 80% by weight of glycerin.

According to another embodiment, a process for making *gynostemma* extract for use in the above compositions is provided, which comprises processing a quantity of raw saponin-containing plant materials comprising at least *gynostemma* plant material in the form of leaves and stems, cut leaves and stems, or milled particles, in an extraction medium comprising water or a mixture of solvents including water, heated to a temperature in the range from around 45 degrees to 120 degrees Centigrade for a time period of at least thirty minutes in a first extraction run to produce an extraction solution containing saponins leaving a raw material residue; draining the first run extraction solution from the raw material residue; adding one or more solvents comprising at least water to the raw plant material residue and heating the mixture at the same temperature range under pressure for a time period of at least thirty minutes in a second extraction run to create a second run extraction solution leaving a raw material residue; draining the second run extraction solution from the raw material residue and combining it with the first run extraction solution; and filtering the extraction solutions in at least one filtering step to obtain a liquid *gynostemma* plant extract containing saponins. The liquid extract may then be dried to form a dried extract powder, which can then be dissolved in water or glycerin, or both water and glycerin, either alone or in combination with other herbal extracts, to produce a surfactant composition as described above.

The amount of saponins in the *gynostemma* extract can be controlled by varying the amount of raw plant material used in the extraction and by purifying the liquid extract to increase the saponin level. In one embodiment, the *gynostemma* extract had a saponin level in the range of 10% to 99% saponins. A level of up to 20% or 30% saponins may be obtained using the extraction process described above. In order to achieve a higher saponin concentration, additional purification steps may be used, such as a purification process using sequential ion-exchange columns.

DETAILED DESCRIPTION

Certain embodiments as disclosed herein provide for combining *gynostemma* extract with other ingredients to produce products such as surfactants for use as cleaning agents, emulsifiers, foaming agents, shaving creams, skin care products, and the like, and for a process for extracting phytocompounds from the *Gynostemma pentaphyllum* plant and/or other plant species of the *gynostemma* genus, including but not limited to the species *G. compressum, G. longipes, G. cardospermum, G. pentagynum, G. pubescens*, either alone or combined with one or more additional plants or herbs containing saponins, to provide *gynostemma* extracts for use in such products.

After reading this description it will become apparent to one skilled in the art how to implement the invention in various alternative embodiments and alternative applications. However, although various embodiments of the present invention are described herein, it is understood that these embodiments are presented by way of example only, and not limitation. As such, this detailed description of various alternative embodiments should not be construed to limit the scope or breadth of the present invention as set forth in the appended claims.

According to one embodiment of the present invention, *gynostemma* extract is used in a surfactant composition by itself or with other saponin-containing herbal extracts such as those derived from soap berry (*sapindus* species), yucca leaf, *panax ginseng*, baical skullcap (*scutellaria baicalensis*), *polygala tenuifolla*, soapwort root (*saponaria* species), *codonopsis pilosulae, camellia sinensis* (green tea), *platycodon grandiflorus, camellia japonica* and *phytolacca esculenta*, all of which exhibit enhanced cleaning effect of a surfactant. The amount of *gynostemma* extract or *gynostemma* and other herbal extracts used may range between 0.1% to 20% by weight of total saponins in water, glycerin, glycerin and water, propylene glycol, butylene glycol, or alcohol to create concentrated or dilute, and foamy cleaning solutions. The gypenoside extract solution can be used for cleaning oils, sebum, dirt and grime on the skin and hair, by formulating into a stable solution base with either a natural or synthetic preservative such as oil of rosemary, rosemary extract, skullcap, parabens or phenoxyethanols, or any combination of the aforesaid materials. Alternatively, the gypenoside solution can be formulated preservative-free using a low-water activity with glycerin, for example, in a glycerin/water solution comprising at least 70% by weight of a glycerin.

In one example, a dried *gynostemma* extract containing 30% gypenoside saponins by weight was dissolved at a rate of 0.1% extract by weight in water or in a solution of 50% glycerin/50% water. The solution was shaken to create an immediate foam-head which rose to several times the height of the original solution. The foam-head was long lasting and durable, and remained at a volume twice that of the original solution after eight hours. It was noted that when only water was used as the solution, the foam volume was similar but the bubbles were noticeably larger in volume. When the extract was applied in a glycerin/water solution, a fine foam head was created in a long-lasting, relatively stable condition over a six hour period.

In another example, a *gynostemma* extract with a minimum of 30% gypenosides or saponins by weight was dissolved in 100 ml of water. This produced a foam head that was approximately double the volume of that for the 0.1% solution as described above, which remained after an 18-hour period. Such a foaming capability is a desired characteristic of a good emulsifying agent. Good foaming ability was found even in hard water.

In one application, a formulation may be made with 1 part of soap berry powdered extract with 4 parts of *gynostemma* extract and 20 parts of glycerin as a carrier. Another formula, which can be adopted for topical application to the human skin, may contain 1 part of *gynostemma* extract, 9 parts soapberry extract and 10 parts glycerin. Another formula may contain 1 part of soap wort extract to 3 parts *gynostemma* extract in a glycerin base. In each case, the dried *gynostemma* extract powder used in the formulation may contain at least 10% by weight of saponins, and in one example each extract contained 10% up to 99% by weight of saponins.

The following are exemplary compositions produced from *gynostemma* extract. In the following examples, the *gynostemma* extract was made using *gynostemma pentaphylla* plant material, but *gynostemma* extract made from other plant species of the *gynostemma* genus could alternatively be used in any of the following examples:

Example 1

A composition containing the following ingredients was prepared in making a natural surfactant: 0.1-0.5 wt % of *gynostemma* extract containing at least 10% by weight of saponins, 98.9-99.5 wt % water, and 0-1.0 wt % of preservatives.

Example 2

A composition containing the following ingredients was prepared in making a natural surfactant for use in a long-lasting, foaming shave cream with all or partial natural ingredients: 0.1-0.5 wt % of *gynostemma* extract containing at least 10% by weight of saponins, 69.5-69.9 wt % glycerin, and 30% water.

Example 3

A composition containing the following ingredients was prepared in making a natural surfactant: 5 wt % of *gynostemma* extract containing at least 10% by weight of saponins, 15 wt % soap berry and 80 wt % glycerin.

Example 4

A composition containing the following ingredients was prepared in making a formula for topical skin care application: 10 wt % of *gynostemma* extract containing at least 10% by weight of saponins, 5 wt % green tea, 5 wt % *panax ginseng* and 80 wt % glycerin.

Example 5

A composition containing the following ingredients was prepared in making a formula to support skin protection, microcirculation in a long-lasting foaming formula, 10 wt % of *gynostemma* extract containing at least 10% by weight of saponins, 5 wt % green tea, 5 wt % soapberry, 56 wt % glycerin and 24 wt % water.

Example 6

A composition containing the following ingredients was prepared in making a surfactant formula: 5 wt % of *gynostemma* extract containing at least 10% by weight of saponins, 5 wt % green tea, 10 wt % soap berry, 5 wt % codonopsis, 60 wt % glycerin and 15 wt % water. In another example, the 5 wt % of *codonopsis* may be replaced with 5 wt % of skullcap.

The *gynostemma* extract compositions described in the above embodiments have distinctive surface tension altering functions, reducing the surface tension of aqueous solutions and allowing foam formation and emulsification with oil, dirt and water insoluble substances, and emulsification with other ingredients in cosmetic or personal care products. *Gynostemma* extract made as described above and dissolved in water or other solvents produces a long-lasting, durable foam head, making it useful for various applications including emulsifying agents and natural surfactants.

The following is a description of one embodiment of a method for making a botanical extract which contains gypenosides and other saponins, polysaccharides, and other phytocompounds, from one or more plant species of the *gynostemma* genus, such as *Gynostemma pentaphyllum, G. compressum, G. longipes, G. cardiospermum, G. pentagynum, G. pubescens*, or other *gynostemma* species, for use in the above compositions. In one embodiment, the extraction is carried out using a liquid extraction medium such as water or water and alcohol, but other solvents such as alcohol, glycerin, propylene glycol, butylene glycol, acetone, hexane, ethyl acetate, methanol, $CO_2$, or any combination of such solvents may be used in alternative embodiments.

In one embodiment, the extraction takes place at elevated temperatures and optionally in a pressurized, closed, continually recirculating system that recirculates continuously until some or all of the saponins and other phytocompounds are pulled out of the plant material. In addition to *gynostemma* genus plants, botanical extracts may be extracted from other plant materials containing saponins in the same way, including, but not limited to, combinations of *gynostemma* extract and one or more plants or herbs such as soap berry (*sapindus* species), *panax ginseng*, baical skullcap (*scutellaria baicalensis*), *polygala tenuifolla*, soapwort root (*saponaria* species), *codonopsis pilosulae, camellia sinensis* (green tea), *platycodon grandiflorus, camellia japonica* and *phytolacca esculenta*.

This process takes several hours for the saponins and other phytocompounds to be "pulled" into the extraction water to form an aqueous solution. Once in solution, saponins and other phytocompounds can be concentrated through successive filtration steps, vacuum evaporation/condensation and spray drying.

The quality of *gynostemma* raw material, particularly saponin level, is monitored and controlled in the raw material used prior to the extraction process so that a minimum value can be achieved for suitable product strength. This is done by testing the *gynostemma* leaf and stem raw material before the extraction process using testing methods and standards from the Pharmacopoeia of the People's Republic of China (PPRC) monograph for *gynostemma*. This allows the gypenoside or saponin level to be tested before the extraction. If the levels are low, more raw leaf and stem material is used. If the level is high, the amount of new leaf and stem material is reduced. The saponin levels are also tested during the process to ensure extraction of saponins into the liquid menstruum, and continual monitoring and adjustments of extraction time, temperature, and pressure is conducted as needed to optimize process efficiency and final saponin levels. The in-process testing measures total saponins as a percentage of total solids so as to meet a minimum value of 10% saponins. The total saponin level may be determined by using one reference standard, in this case gypenoside, by a UV-Vis analytical method.

In one embodiment, the process is controlled so that the final product as *gynostemma* powder extract has a range of 10% to 99% saponins (gypenoside and other saponins), with a purification process after the extraction steps to produce saponin levels higher than 30%. A purification process using sequential ion-exchange resin columns may be used to increase the saponin level to up to 99%. A suitable purification process is described in Li H, Lee J H, Ha J M. Effective purification of ginsenosides from cultured wild ginseng roots, red ginseng, and white ginseng with macroporous resins. J Microbiol Biotechnol. 2008 November; 18(11): 1789-91. This reference describes a resin purification process used to concentrate ginsenosides, which are structurally and chemically similar to gypenosides, and thus a similar process can be used to increase the saponin level in the *gynostemma* extract which is produced in the above process.

The following are exemplary processes for the extraction of the saponins from raw *gynostemma* plant material:

Process 1:

In one example, *gynostemma* extracts are produced by placing fresh or dry *gynostemma pentaphylla* leaves and stems in an extraction vessel, together with a solution consisting of water, ethanol or a combination of water and ethanol for an extraction period of approximately thirty minutes to four hours in a first extraction run at a temperature range from around 45 degrees to 120 degrees Centigrade. The solution may be continually re-circulated in a pressurized, closed system during the extraction. Then the first run extraction solution (menstruum) is drained to a storage tank. This step is followed by a second extraction run by adding an equal amount of solution (water, ethanol or a combination of water and ethanol) to the remaining *gynostemma* leaves and stems in the extraction vessel between one to four hours and heated at a similar temperature range. Thereafter, the extraction solutions are combined and filtered, preferably by a pressure filter, a centrifuge or a combination thereof, to obtain a liquid extract. The liquid extract is then dried to obtain a solid material of which the levels of saponins (gypenosides plus other saponins) ranges from a minimum of 10% by weight and up to 99% by weight (with a purification process as described above used to obtain saponin levels of greater than 30% by weight). Although *gynostemma pentaphylla* leaves and stems are used in the foregoing example, other plants of the *gynostemma* genus may be used in the same extraction process with similar results, such as *G. compressum, G. longipes, G. cardiospermum, G. pentagynum, G. pubescens*, or other plants of the *gynostemma* species.

Process 2:

Saponins or gypenosides are extracted from *gynostemma* plant material, such as *gynostemma pentaphylla* or other *gynostemma* genus plants, by using water, ethanol or a combination of water and ethanol. Approximately 50 kilograms of *gynostemma* leaves and stems are milled to a small particle size of 0.5 cm to 10 cm or cut in pieces of length around 10 cm to 50 cm, and added to an extractor vessel with 200 to 1000 liters of solution consisting of water, ethanol or a combination of water and ethanol. The mixture is heated between one to six hours under a pressure of 0-0.05 mpa (0-7.25 psi) after which the extraction solution is drained to a storage tank.

The remaining solid mixtures are processed in a second extraction run by adding an equal or less amount of solution (water, ethanol or a combination of water and ethanol) between 0.5 hour to 4 hours and heated at a similar temperature range, under a pressure of 0-0.05 mpa (0-7.25 psi).

A third extraction phase may be undertaken if desirable to remove any remaining saponins or gypenosides from the remaining solid materials. This third extraction phase can be applied for a duration of 0.5 to 2 hours by adding an equal or less amount of solution (water, ethanol or a combination of water and ethanol) and heating the mixture at a similar temperature range, under a pressure of 0-0.05 mpa (0-7.25 psi).

Following the extraction steps, the extracted liquids are mixed in a mixing vessel, filtered and dried by appropriate means known in the art to remove any herb residue and water and/or ethanol contents.

Thereafter, decolorizing is undertaken by settling out some of the brown colored residue, such as tannins, with appropriate means, for example, activated charcoal, ion-exchange separators or by a combination of these means, with or without filtering. As an alternative means, color residues may be allowed to settle by gravity to the lower portion of the mixing tank while the extraction liquid is undisturbed.

Thereafter, *gynostemma* extract is dried to result in a solid state. As an alternative, the extract may be mixed with water, propylene glycol, butylene glycol, glycerin, ethanol, glycerol, or any combination of such substances in a liquid, gel or in other forms.

Depending on the number of batches of raw herbs needed to be extracted to achieve the desired concentration of saponins in the final extract, and the combination of the extract with other carrier materials, the levels of total saponins in the final dried powder extract can range from 10% to 99% by weight or from 0.01% to 20% after the concentrated form is mixed into a suitable carrier liquid, gel or other format.

As an alternative composition, with similar steps as described above, the amount of raw materials used in the extractor may be between 25 kilogram and 600 kilograms and the solution consisting of water, ethanol or a combination of water and ethanol in the extraction phases may range between 100 liters and 12,000 liters.

The range of powdered *gynostemma* extract dissolved into a liquid form solution, comprised of one or more of water, propylene glycol, butylene glycol, glycerin, ethanol, or mixtures thereof, may be between 0.01%-20% by weight.

It has been observed that the surfactant characteristic of the *gynostemma* extract is exhibited during the extraction of *gynostemma* as the extractor vessel becomes filled with a long-lasting foam head. The final weight of the product may be between 1% to 50% of the original raw materials used.

This final weight divided by the original weight of raw plant material determines the extraction ratio and the concentration of active compounds of saponins. With a range of 0.2% to 7% saponins in the starting material, a 4:1 extraction ratio may produce a *gynostemma* extract containing a range of 0.8% to 28% by weight of saponins. With a 10:1 extraction ratio, the same raw material may yield between 20 to 70% by weight of saponins.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

REFERENCES

Incorporated Herein by Reference

Chang C K, Chang K S, Lin Y C, Liu S Y, Chen C Y. Hairy root cultures of *Gynostemma pentaphyllum* (Thunb.) Makino: a promising approach for the production of gypenosides as an alternative of ginseng saponins Biotechnol Lett. 2005 August; 27(16):1165-9.

Ding S L, Zhu Z Y. Gycomoside I: a new dammarane saponin from *Gynostemma compressum*. Planta Med. 1993 August; 59(4):373-5.

Ding S L, Zhu Z Y. [Studies on chemical constituents of *Gynostemma compressum*]. Yao Xue Xue Bao. 1993; 28(5):364-9.

Guo X L, Wang T J, Bian B L. [Studies on the chemical constituents of *Gynostemma longipes* C. Y. Wu]. Yao Xue Xue Bao. 1997 July; 32(7):524-9.

Huang T H, Tran V H, Roufogalis B D, Li Y. Gypenoside XLIX, a naturally occurring gynosaponin, PPAR-alpha dependently inhibits LPS-induced tissue factor expression and activity in human THP-1 monocytic cells. Toxicol Appl Pharmacol. 2007 Jan. 1; 218(1):30-6. Epub 2006 Oct. 25.

Hu L, Chen Z, Xie Y. New triterpenoid saponins from *Gynostemma pentaphyllum*. J Nat Prod. 1996 December; 59(12):1143-5. Guo X L, Wang T J, Bian B L. [Studies on the chemical constituents of *Gynostemma longipes* C. Y. Wu]. Yao Xue Xue Bao. 1997 July; 32(7):524-9.

Hui R H, Hou D Y, Li T C, Liu X Y. [Simultaneous determination of total flavone and total saponin in *gynostemma pentaphyllum* by signal multiplier spectrophotometry]. Guang Pu Xue Yu Guang Pu Fen Xi. 2006 September; 26(9):1753-6.

Kao T H, Huang S C, Inbaraj B S, Chen B H. Determination of flavonoids and saponins in *Gynostemma pentaphyllum* (Thunb.) Makino by liquid chromatography-mass spectrometry. Anal Chim Acta. 2008 Sep. 26; 626(2):200-11. Epub 2008 Aug. 8.

Li H, Lee J H, Ha J M. Effective purification of ginsenosides from cultured wild ginseng roots, red ginseng, and white ginseng with macroporous resins. J Microbiol Biotechnol. 2008 November; 18(11):1789-91.

Liu F, Ren D, Guo D A, Pan Y, Zhang H, Hu P. Method development for gypenosides fingerprint by high performance liquid chromatography with diode-array detection and the addition of internal standard. Chem Pharm Bull (Tokyo). 2008 March; 56(3):389-93.

Tanaka O, Han E C, Yamaguchi H, Matsuura H, Murakami T, Taniyama T, Yoshikawa M. Saponins of plants of *Panax* species collected in Central Nepal, and their chemotaxonomical significance. III. Chem Pharm Bull (Tokyo). 2000 June; 48(6):889-92.

Wei J, Chen Y, Cao S. [Saponins in the fruit pedicels of *Panax notoginseng* (Burk.) F. H. Chen (continue)]. Zhongguo Zhong Yao Za Zhi. 1992 October; 17(10):611-3, 639-40 concl.

Xiang W J, Guo C Y, Ma L, Hu L H. Dammarane-type glycosides and long chain sesquiterpene glycosides from *Gynostemma yixingense*. Fitoterapia. 2009 Sep. 23. [Epub ahead of print]

Yang Z, Chen Q, Hu L. Dammarane-type glycosides from *Gynostemma pubescens*. Phytochemistry. 2007 July; 68(13):1752-61. Epub 2007 Jun. 15.

Yin F, Hu L, Lou F, Pan R. Dammarane-type glycosides from *Gynostemma pentaphyllum*. J Nat Prod. 2004 June; 67(6): 942-52.

Yin F, Zhang Y N, Yang Z Y, Hu L H. Nine new dammarane saponins from *Gynostemma pentaphyllum*. Chem Biodivers. 2006 July; 3(7):771-82.

Yin F, Zhang Y, Yang Z, Cheng Q, Hu L. Triterpene saponins from *Gynostemma cardiospermum*. J Nat Prod. 2006 October; 69(10):1394-8.

The invention claimed is:

1. A *gynostemma* extract based natural surfactant composition consisting essentially of:
   0.1% to 20% by weight of *gynostemma* extract which is used as cleaning agent, foaming agent and emulsifier;
   a carrier liquid comprising water and glycerin; and
   three additional saponin-containing extracts comprising about 5% by weight of green tea, about 10% by weight of soap berry, and about 5% by weight of codonopsis, and the carrier liquid comprises about 15% by weight of water and about 60% by weight of glycerin.

2. The composition of claim 1, wherein the *gynostemma* extract contains at least 10% by weight of saponins.

3. The composition of claim 1, comprising 5% by weight of *gynostemma* extract containing at least 10% by weight of saponins for making a cleaning surfactant formula.

4. The composition of claim 3, wherein the 5% by weight of codonopsis is replaced with 5% by weight of skullcap.

5. The composition of claim 1, comprising about 0.1%-0.5% by weight of *gynostemma* extract containing at least 10% by weight of saponins to be used as a foaming agent.

6. The composition of claim 5, wherein the *gynostemma* extract contains about 30% gypenoside saponins.

7. The composition of claim 1, comprising about 10% by weight of *gynostemma* extract containing at least 10% by weight of saponins.

* * * * *